US008758231B2

(12) United States Patent
Bunch et al.

(10) Patent No.: US 8,758,231 B2
(45) Date of Patent: Jun. 24, 2014

(54) ACCESS SHEATH WITH ACTIVE DEFLECTION

(75) Inventors: Tyler J. Bunch, Bloomington, IN (US); Walter N. Ryan, Greenville, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 117 days.

(21) Appl. No.: 13/319,850

(22) PCT Filed: May 12, 2010

(86) PCT No.: PCT/US2010/034536
§ 371 (c)(1),
(2), (4) Date: Nov. 10, 2011

(87) PCT Pub. No.: WO2010/132560
PCT Pub. Date: Nov. 18, 2010

(65) Prior Publication Data
US 2012/0053415 A1    Mar. 1, 2012

Related U.S. Application Data
(60) Provisional application No. 61/178,189, filed on May 14, 2009.

(51) Int. Cl.
A61B 1/00    (2006.01)
A61B 1/005   (2006.01)
A61B 1/008   (2006.01)

(52) U.S. Cl.
CPC .............. *A61B 1/005* (2013.01); *A61B 1/0055* (2013.01); *A61B 1/008* (2013.01)
USPC ........................... 600/141; 600/139; 600/142

(58) Field of Classification Search
USPC ............ 600/140, 141, 149, 114, 139; 348/45; 604/535
See application file for complete search history.

(56) References Cited

U.S. PATENT DOCUMENTS 4,838,339 A * 6/1989 French ................... 164/340
4,997,424 A   3/1991 Little
(Continued)

FOREIGN PATENT DOCUMENTS

EP    0 815 895 A1    1/1998
EP    1 484 003 A1    12/2004
(Continued)

OTHER PUBLICATIONS

"Introducing the Next Generation of Ureteral Access Sheaths from Cook," Flexor Ureteral Access Sheath, copyright Cook Urological Inc. 2002, 4 pages.

(Continued)

*Primary Examiner* — Alireza Nia
*Assistant Examiner* — Timothy J Neal
(74) *Attorney, Agent, or Firm* — Brinks Gilson & Lione

(57) ABSTRACT

In at least one embodiment of the present invention, an access sheath for positioning in a patient's body is provided. The access sheath comprises an elongated member having a proximal portion extending to a distal portion and a plurality of lumens formed therethrough including a working lumen and a first additional lumen. The first additional lumen is configured to receive an optical system or an irrigation system. The proximal portion has a stiffening section that includes a first coil and one of a braiding and a second coil which are disposed about the working lumen in concentric relationship with each other. The distal portion has a tip and a first deflection section and a second deflection section. The first deflection section is proximal to the tip and distal to the second deflection section. The first deflection section is configured to be actuated to bend at a first angle to position the tip. The second deflection section is configured to bend at a second angle to reposition the tip.

9 Claims, 8 Drawing Sheets

(56) References Cited

U.S. PATENT DOCUMENTS

| | | |
|---|---|---|
| 5,188,606 A | 2/1993 | Maloney et al. |
| RE34,502 E | 1/1994 | Webster, Jr. |
| 5,304,142 A | 4/1994 | Liebl et al. |
| 5,380,304 A | 1/1995 | Parker |
| 5,429,616 A | 7/1995 | Schaffer |
| 5,431,168 A | 7/1995 | Webster, Jr. |
| 5,599,305 A | 2/1997 | Hermann et al. |
| 5,700,253 A | 12/1997 | Parker |
| 5,704,898 A | 1/1998 | Kokish |
| 5,755,760 A | 5/1998 | Maguire et al. |
| 5,772,578 A | 6/1998 | Heimberger et al. |
| 5,843,031 A | 12/1998 | Hermann et al. |
| 5,865,800 A | 2/1999 | Mirarchi et al. |
| 5,897,529 A | 4/1999 | Ponzi |
| 6,064,905 A | 5/2000 | Webster, Jr. et al. |
| 6,066,125 A | 5/2000 | Webster, Jr. |
| 6,066,126 A | 5/2000 | Li et al. |
| 6,102,887 A | 8/2000 | Altman |
| 6,123,699 A | 9/2000 | Webster, Jr. |
| 6,183,463 B1 | 2/2001 | Webster, Jr. |
| 6,198,974 B1 | 3/2001 | Webster, Jr. |
| 6,203,507 B1 | 3/2001 | Wadsworth et al. |
| 6,210,362 B1 | 4/2001 | Ponzi |
| 6,210,407 B1 | 4/2001 | Webster |
| 6,240,231 B1 | 5/2001 | Ferrera et al. |
| 6,277,108 B1 | 8/2001 | McBroom et al. |
| 6,319,244 B2 | 11/2001 | Suresh et al. |
| 6,338,725 B1 | 1/2002 | Hermann et al. |
| 6,346,099 B1 | 2/2002 | Altman |
| 6,352,531 B1 | 3/2002 | O'Connor et al. |
| 6,398,776 B1 | 6/2002 | Sekino et al. |
| 6,419,641 B1 | 7/2002 | Mark et al. |
| 6,458,076 B1 | 10/2002 | Pruitt |
| 6,471,648 B1 | 10/2002 | Gamelsky et al. |
| 6,475,184 B1 | 11/2002 | Wang et al. |
| 6,500,167 B1 | 12/2002 | Webster, Jr. |
| 6,503,193 B1 * | 1/2003 | Iwasaki et al. ............... 600/140 |
| 6,537,480 B1 | 3/2003 | Becker et al. |
| 6,551,302 B1 | 4/2003 | Rosinko et al. |
| 6,554,794 B1 | 4/2003 | Mueller et al. |
| 6,571,131 B1 | 5/2003 | Nguyen |
| 6,595,982 B2 | 7/2003 | Sekino et al. |
| 6,613,017 B1 | 9/2003 | Mickley |
| 6,638,213 B2 * | 10/2003 | Ogura et al. ............... 600/148 |
| 6,641,564 B1 | 11/2003 | Kraus |
| 6,712,789 B1 | 3/2004 | Lange et al. |
| 6,716,223 B2 | 4/2004 | Leopold et al. |
| 6,723,070 B1 | 4/2004 | Arai et al. |
| 6,796,976 B1 | 9/2004 | Chin et al. |
| 6,855,106 B2 | 2/2005 | May et al. |
| 6,893,421 B1 | 5/2005 | Larson et al. |
| 6,951,555 B1 | 10/2005 | Suresh et al. |
| 7,122,020 B2 | 10/2006 | Mogul |
| 7,135,015 B2 | 11/2006 | Dulak et al. |
| 8,366,607 B2 * | 2/2013 | Sullivan et al. ............... 600/149 |
| 2001/0034514 A1 | 10/2001 | Parker |
| 2001/0037084 A1 | 11/2001 | Nardeo |
| 2002/0115983 A1 | 8/2002 | Sekino et al. |
| 2002/0161353 A1 | 10/2002 | Kortellinq |
| 2003/0004460 A1 | 1/2003 | Bedell |
| 2003/0135156 A1 | 7/2003 | Bencini et al. |
| 2003/0135198 A1 | 7/2003 | Berhow et al. |
| 2003/0236493 A1 | 12/2003 | Mauch |
| 2004/0015138 A1 | 1/2004 | Currier et al. |
| 2004/0044350 A1 | 3/2004 | Martin et al. |
| 2004/0054377 A1 | 3/2004 | Foster et al. |
| 2004/0092962 A1 | 5/2004 | Thornton et al. |
| 2004/0176744 A1 | 9/2004 | Lanoe et al. |
| 2004/0193112 A1 | 9/2004 | Glazier et al. |
| 2004/0220549 A1 | 11/2004 | Dittman et al. |
| 2004/0236346 A1 | 11/2004 | Parker |
| 2004/0242966 A1 | 12/2004 | Barry et al. |
| 2005/0004515 A1 | 1/2005 | Hart et al. |
| 2005/0043712 A1 * | 2/2005 | Devens ............... 604/525 |
| 2005/0065467 A1 | 3/2005 | Pudelko et al. |
| 2005/0065474 A1 | 3/2005 | Larson et al. |
| 2005/0165366 A1 | 7/2005 | Brustad et al. |
| 2005/0192606 A1 | 9/2005 | Paul, Jr. et al. |
| 2005/0222581 A1 | 10/2005 | Fischer, Jr. et al. |
| 2005/0222664 A1 | 10/2005 | Parker |
| 2005/0228479 A1 | 10/2005 | Pavcnik et al. |
| 2005/0256452 A1 | 11/2005 | DeMarchi et al. |
| 2006/0178560 A1 * | 8/2006 | Saadat et al. ............... 600/114 |
| 2006/0200000 A1 | 9/2006 | Sato et al. |
| 2007/0066869 A1 * | 3/2007 | Hoffman ............... 600/121 |
| 2007/0078455 A1 | 4/2007 | Rashidi |
| 2007/0203474 A1 | 8/2007 | Ryan et al. |

FOREIGN PATENT DOCUMENTS

| | | |
|---|---|---|
| WO | WO 91/01772 | 2/1991 |
| WO | WO 02/11807 A2 | 2/2002 |
| WO | WO 03/090835 A1 | 11/2003 |
| WO | WO 2004/096015 A2 | 11/2004 |
| WO | WO 2004/103434 A2 | 12/2004 |
| WO | WO 2005/072806 A2 | 8/2005 |
| WO | WO 2005/123169 A1 | 12/2005 |
| WO | WO 2006/110275 A2 | 10/2006 |

OTHER PUBLICATIONS

"The Polyscope," from http://www.matricsmedical.com/PRODUCTS/index_solution.html. Matrics Medical, printed Nov. 11, 2005, 4 pages.

International Search Report from PCT International application No. PCT/US2007/000073 dated Aug. 20, 2007 (6 pages).

International Search Report from PCT International application No. PCT/US2007/000073 dated Jul. 24, 2008 (7 pages).

EPO Examination Report dated May 27, 2010 for EP Application No. EP07716241.0.

* cited by examiner

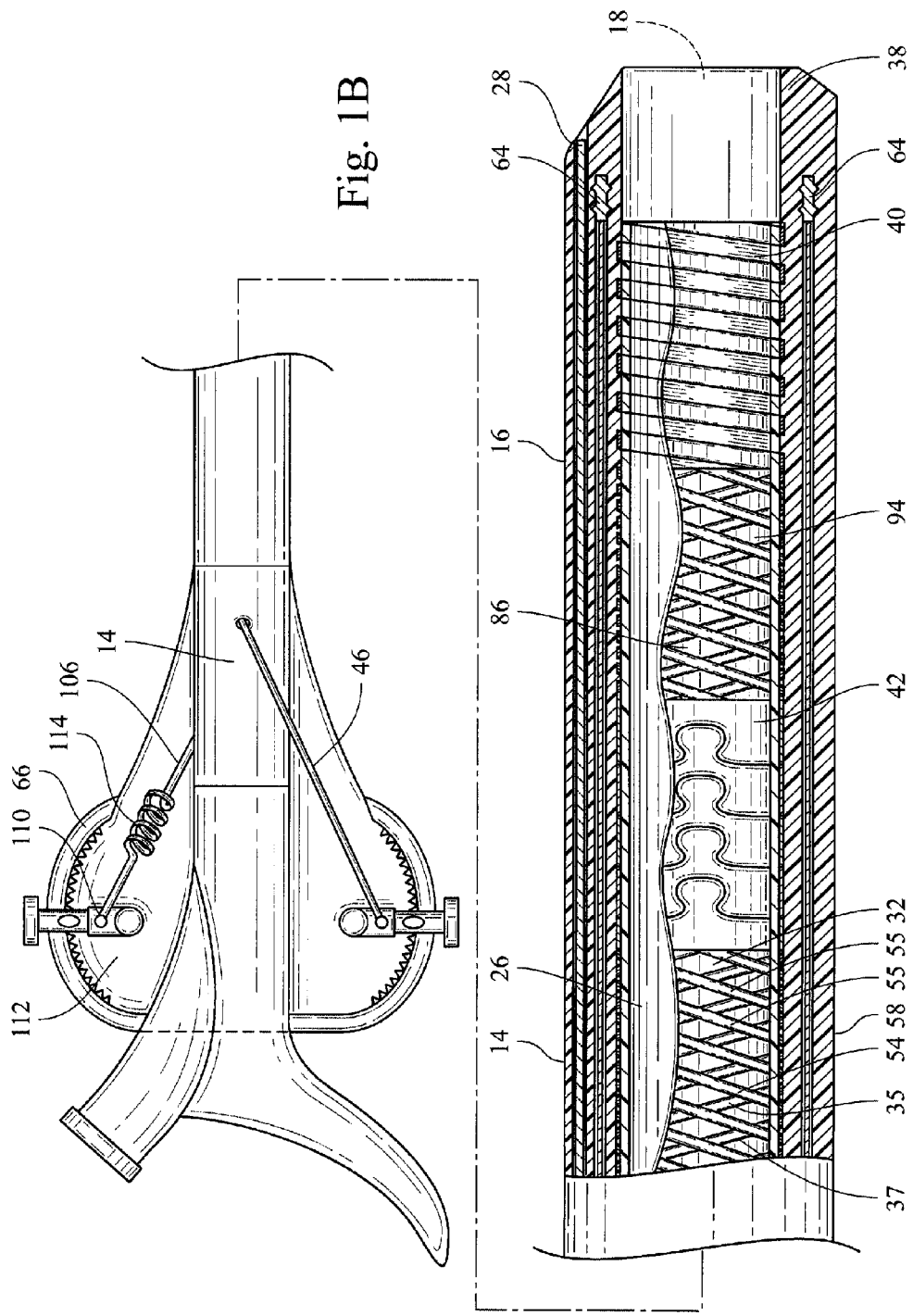

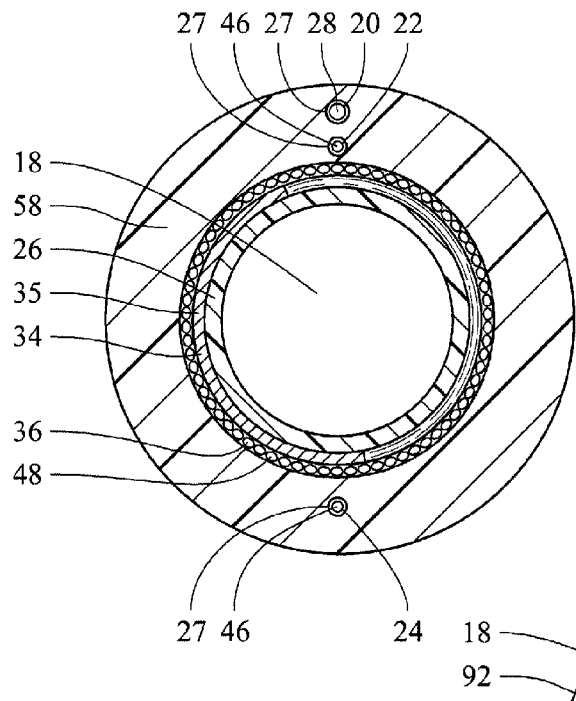
Fig. 1C(1)
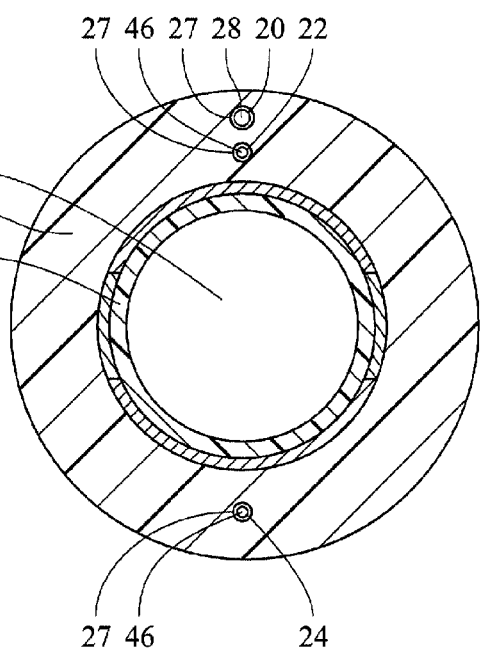
Fig. 1D(1)
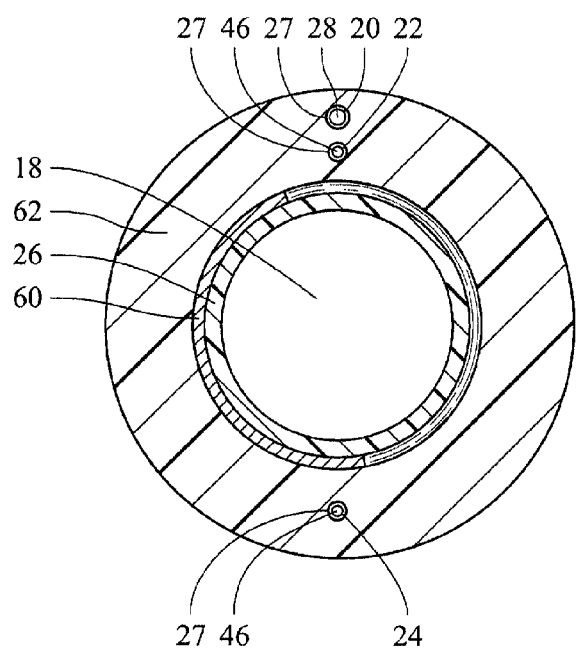
Fig. 1E(1)

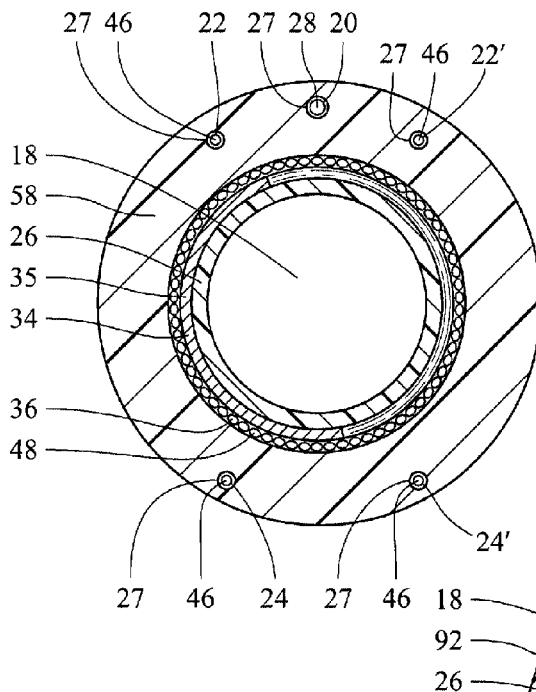
Fig. 1C(2)
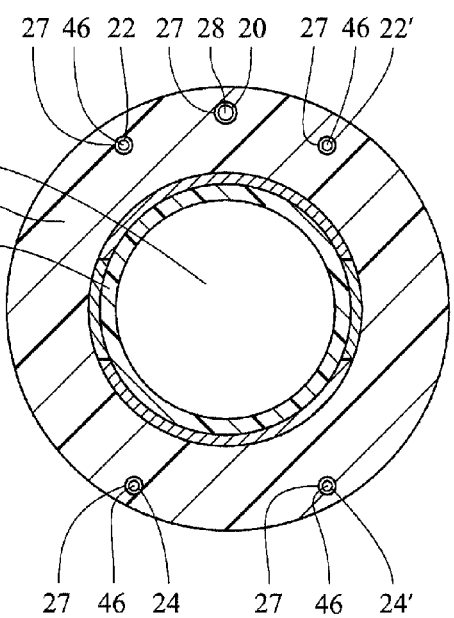
Fig. 1D(2)
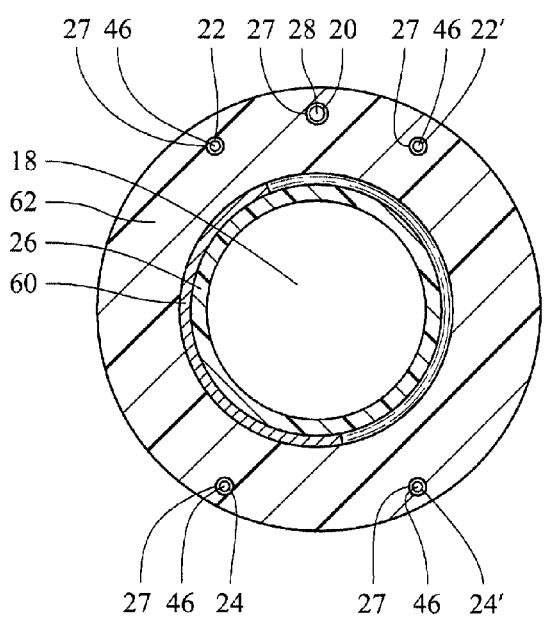
Fig. 1E(2)

ACCESS SHEATH WITH ACTIVE DEFLECTION

CROSS REFERENCE TO RELATED APPLICATIONS

This application is related to and claims the benefit of priority to PCT/US2010/034536, filed on May 12, 2010 which application claims priority to and all available benefits of U.S. Provisional Patent Application Ser. No. 61/178,189, filed May 14, 2009, entitled "ACCESS SHEATH WITH ACTIVE DEFLECTION," both of which are hereby incorporated by reference in their entirety.

BACKGROUND OF THE INVENTION

1. Field of the Invention

The present invention relates to medical devices. More particularly, the invention relates to the field of endoscopic and laparoscopic medical devices used primarily in minimally-invasive surgery.

2. Background of the Invention

Access sheaths, such as ureteral access sheaths, may be used to gain access to body cavities in lumens during endoscopic and laparoscopic surgery, and by other procedures that generally use minimally invasive techniques. Thus, ureteral access sheaths may be used with an endoscope for finding and removing kidney stones, and may be used in other applications, such as access to bile ducts. Other applications for which an access sheath has been used include vascular procedures, as well as procedures requiring gastro-intestinal access, uterine access, and bronchial access. Thus, sheaths may be used in combination with endoscopes, hysteroscopes, sigmoidoscopes, bronchoscopes, and many other types of instruments for minimally-invasive techniques.

Using a sheath provides for a way to protect the tissues of a patient during a procedure. For instance, if a kidney stone is to be removed, a retrieval basket may require many passages back and forth across the patient's ureter to remove stone fragments. Passing the basket through the access sheath instead of the ureter itself avoids trauma to the ureter and the surrounding tissues.

One problem that is common to many procedures in which these devices are used is that more and more is expected from the surgeon and the operating team. For instances, now that an access sheath may be used to access across a ureter, the surgeon may wish to use the sheath for access not only for an endoscope, but also for multiple endoscopic instruments, such as a retrieval basket, a stone "blocker" or back stop, a fiberoptic laser to break up stones, a safety wire, an operating wire, or a system to provide irrigation or to instill contrast agents. While all of these systems are desirable, it is difficult to operate them all at the same time and through the same access sheath. Thus, the surgeon may also pass instruments through the endoscope as well as the access sheath.

Removal of kidney stones and other calculi within body cavities may be accomplished with an endoscope or other expensive piece of equipment. An endoscope is inserted into the patient, desirably using a body passageway, such as a ureter or a blood vessel. An endoscope includes an integral optical system, a working channel, and a way to maneuver the endoscope so that the surgeon can accomplish a therapeutic or diagnostic procedure. The surgeon positions the endoscope so that the surgeon can observe the desired body part of the patient using the optical system, with irrigation if necessary. The surgeon then uses at least one instrument, such as a laser or a grasper, to break up and remove objects in the body passageway. The endoscope may also be used for diagnostic purposes, such as for observing the desired portion of the patient and then taking a biopsy sample.

Flexible endoscopes are very expensive pieces of equipment. When this application refers to endoscopes, primarily flexible endoscopes are intended. They may cost from $10,000 to $20,000 and are typically used for no more than 10-15 procedures before they require a $3,000 to $5,000 overhaul. Part of the problem may be the very extensive cleaning and sterilization that is required after each use on a patient. After the overhaul, the endoscope may typically be serviceable for only another 10 procedures before requiring an additional overhaul. Thus, endoscopes are very expensive and they require a great deal of attention and maintenance. Because damage is not always apparent to hospital personnel, the need for repair or overhaul on the endoscope may become obvious during a medical procedure, causing a delay in completing the procedure. Thus, it may be necessary to keep multiple endoscopes in stock to ensure their availability at all times.

What is needed is a more effective way to access body cavities during endoscopic and laparoscopic surgery including an ability to navigate through tortuous body passageways and cavities while allowing for important access functions.

BRIEF SUMMARY OF THE INVENTION

In at least one embodiment of the present invention, an access sheath for being positioned in a patient's body by an interventionalist is provided. The access sheath comprises an elongated member having a proximal portion extending to a distal portion and a plurality of lumens formed therethrough. The lumens include a working lumen and a first additional lumen. The first additional lumen is configured to receive one of an optical system and an irrigation system. The proximal portion has a stiffening section that includes a first coil and one of a first braiding and a second coil. The first coil and the one of the first braiding and the second coil are disposed about the working lumen in concentric relationship with each other. The distal portion has a tip, a first deflection section and a second deflection section. Proximal to the tip is the first deflection section which is distal to the second deflection section. The first deflection section is configured to be actuated by the interventionalist to bend at a first angle to position the tip. The second deflection section is configured to bend at a second angle to reposition the tip.

In at least one other embodiment of the present invention, a medical kit for providing internal access to a patient's body is provided. The kit comprises an access sheath as discussed in the foregoing paragraph and an optical system for positioning in the first additional lumen for viewing inside the patient's body.

An example of a method for positioning an access sheath in a patient's body in accordance with the present invention is provided. The method comprises actuating a first deflection section of a distal portion of an elongated member to bend at a first angle to position a tip of the distal portion. The elongated member has a proximal portion with a stiffening section. The stiffening section includes a first coil and one of a first braiding and a second coil in concentric relationship with each other to facilitate positioning of the tip. A portion of the elongated member is contacted with part of the patient's body to bend a second deflection section of the distal portion at a second angle to reposition the tip.

Further objects, features, and advantages of the present invention will become apparent from consideration of the

BRIEF DESCRIPTION OF THE DRAWINGS

FIG. 1b is tear-away side view of an access sheath in accordance with another embodiment of the present invention;

FIG. 1c1 is one example of a cross-section of the access sheath depicted in FIG. 1a;

FIG. 1c2 is another example of a cross-section of the access sheath depicted in FIG. 1a;

FIG. 1d1 is one example of a cross-section of the access sheath depicted in FIG. 1a;

FIG. 1d2 is another example of a cross-section of the access sheath depicted in FIG. 1a;

FIG. 1e1 is one example of a cross-section of the access sheath depicted in FIG. 1a;

FIG. 1e2 is another example of a cross-section of the access sheath depicted in FIG. 1a;

DETAILED DESCRIPTION OF THE INVENTION

Figure 1A:
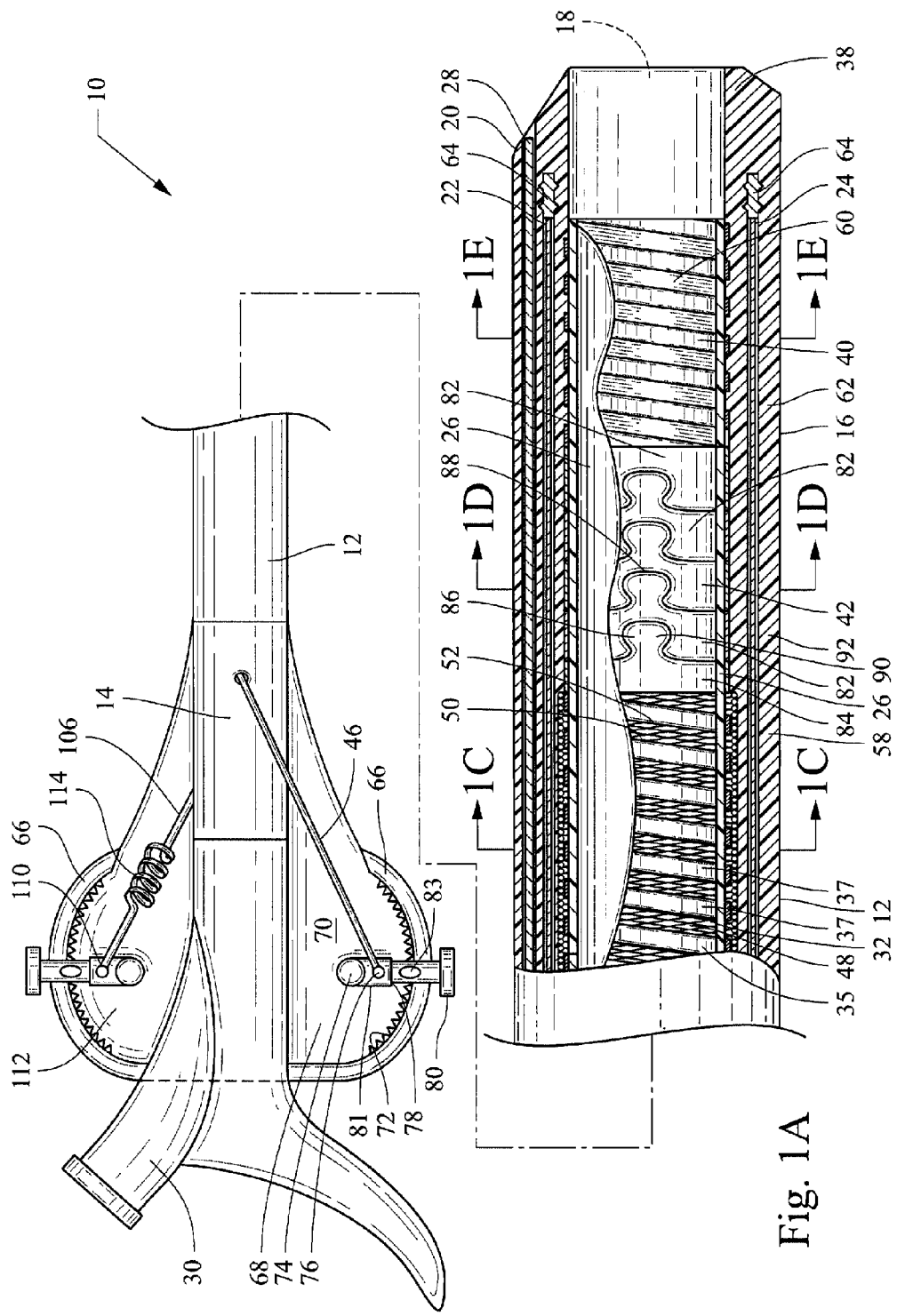
FIG. 1a is a tear-away side view of an access sheath in accordance with an embodiment of the present invention.

Detailed embodiments of the present invention are disclosed herein. It is understood, however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis for the claims and/or teaching one skilled in the art to practice the present invention.

Examples of the present invention seek to overcome some of the concerns associated with accessing body pathways and cavities, which may be tortuous, during endoscopic and laparoscopic surgery.

Embodiments of the present invention concern a steerable access sheath that may be used for endoscopic or laparoscopic surgical procedures. The differences between an access sheath and an endoscope are subtle. An endoscope, especially a flexible endoscope, is an optical instrument that transmits light and carries images back to an observer through a flexible bundle of small (about 10 micrometers) transparent fibers. Such an endoscope is used to inspect interior portions of the body, may be equipped with mechanisms for steering, and may have additional lumens for allowing sampling and/or operative instruments along their axis to the internal site.

Thus, an endoscope is first and foremost a medical device for diagnostic procedures, and is defined as an optical instrument. The instrument may or may not have a steering mechanism and it may or may not have an additional lumen, i.e., a working channel, for sampling or operating instruments. Endoscopes are typically narrow, with an outer diameter from about 3.0 to 6.0 millimeters (mm). In urology, the "working channel" may be from about 0.8 to 1.2 mm in diameter (about 2.4 French (Fr.) to 3.6 Fr.). In contrast, many access sheaths currently sold having a working channel with a minimum of about 9.5 Fr. up to 14 Fr., with an outer diameter from about 11 Fr. (3.7 mm) to about 16 F. (5.4 mm). An access sheath is not primarily an optical instrument and may or may not use an optical system.

In applying the principles of the present inventions, the access sheath comprises an elongated member having two deflection sections for positioning and repositioning its distal tip. The access sheath also includes a stiffening section that includes at least two concentrically positioned reinforcement layers about a working lumen which enhance stiffness and concentrate bending forces at the deflection sections. The stiffening section facilitates bending of the deflection sections to position and/or reposition the tip for preferably maneuvering through even tortuous body passageways and cavities during endoscopic and laparoscopic surgery.

Referring to FIGS. 1a and 1c1-1e2, an access sheath 10 for positioning in a patient in accordance with at least one embodiment of the present invention is provided. The access sheath 10 comprises an elongated member 12 that has a proximal portion 14 extending to a distal portion 16. Defined by the access sheath 10 are several lumens including a large or working lumen 18 and a plurality of smaller additional lumens 20, 22 and 24 as illustrated in FIGS. 1c1, 1d1 and 1e1, or 20, 22, 22', 24 and 24' as illustrated in FIGS. 1c2, 1d2 and 1e2 for example. The working lumen 18 is lined with a layer of lubricious polymer 26, such as a fluoropolymer liner, e.g., polytetrafluoroethylene (PTFE) or Teflon®. Preferably, the additional lumens 20, 22 and 24 are lined with a fluoropolymer liner 27 or other lubricious material on its inner surface. Polyethylene, polypropylene or other polymer may be used instead of a fluoropolymer.

The working lumen 18 is desirably larger than the additional lumens 20, 22 and 24 and may be used for therapeutic or diagnostic purposes, such as removing kidney or bile stones, or for collecting a biopsy sample. In these instances, the first additional lumen 20 may be used to receive an optical system 28 which is for guiding the interventionalist (e.g. physician or other medical professional) during a therapeutic procedure. The optical system 28 may be connected by a connector 30 on the proximal portion 14 of the access sheath 10. There may be an additional lumen or lumens (not shown) for an irrigation system to aid the optical system 28, or alternatively, the first additional lumen 20 may be used for the irrigation system.

The optical system 28 preferably includes a lens and an optical fiber for transmitting light to the lens so that an image is transmitted from the lens to the interventionalist. An eyepiece and a light source are also desirable components but may or may not be part of the removable optical assembly 28. Components for an optical system 28 may be purchased, for example, from Fujikura America, Atlanta, Ga. These include image fibers, light sources and light guides, fiber scopes with image fibers, digital optics (e.g. including CMOS and CCD), eyepieces, and lens. These components are relatively very thin, useful, and inexpensive. Other suitable optical systems known to those skilled in the art may alternatively be used. The access sheath 10 is desirably sufficiently inexpensive for one time only use.

The proximal portion 14 of the elongated member 12 has a stiffening section 32. The stiffening section 32 comprises at least two reinforcement layers including a first reinforcement layer 34 and a second reinforcement layer 36. The reinforcement layers 34 and 36 are disposed about the working lumen 18 and are in concentric relationship with each other.

In one embodiment, the first reinforcement layer 34 is formed of a coil wrapping 35 comprising a plurality of flat wire turns 37 which, for example, are positioned at an acute angle to the working lumen 18 and are uniformly spaced apart in the range of about 0.005 inches to 0.015 inches between the turns. The coil wrapping 35 may be formed, for example, from 0.003 inch thick by 0.012 inch wide flat stainless steel wire. The coil wrapping 35 is compression fitted around the outer surface of the inner liner 26 of the working lumen 18.

In one embodiment, the second reinforcement layer 36 is formed from a braiding 48 that is compression fitted to and wrapped around the first reinforcement layer 34. The braiding 48 may be, for example, constructed of stainless steel wire arranged in warp and weft directions 50 and 52 to form a bi-directional woven pattern. It is believed that the bi-direction pattern of the braiding 48 enhances stiffness of the stiffening section 32 by providing bi-directional stress distribution.

In an alternative embodiment as illustrated in FIG. 1b, the second reinforcement layer 36 is formed from a second coil wrapping 54 that is compression fitted to and wrapped around the first coil wrapping 35. The second coil wrapping 54 may be constructed similar to the first coil wrapping 35 but with its flat wire turns 55 positioned at an angle to the flat wire turns 37 of the first coil wrapping 35 to provide bi-directional stress distribution for enhancing stiffness of the stiffening section 32.

Referring also to FIGS. 1a and 1c1-1e2, a polymeric layer or liner 58 is disposed about the second reinforcement layer 36 and forms an exterior layer of the stiffening section 32. The exterior liner 58 may be made from a polymeric material, such as silicone, nylon or urethane. Other medically acceptable thermoplastic or thermoset material may also be used either separately or in combination, including PTFE, a fluoropolymer, polyethylene, polypropylene, acetyl, urethane, and others.

At the distal end of the distal portion 16, the access sheath 10 has a tip 38. The working lumen 18 is formed through the tip 38 for providing access to a patient's body when the distal portion 16 of the sheath 10 is positioned in the patient. The distal portion 16 also has at least two deflection sections including a first deflection section 40 and a second deflection section 42. The deflection sections 40 and 42 bend relative to the stiffening section 32 to position and reposition the tip 38 in the patient's body. The first deflection section 40 is proximal to the tip 38 and is distal to the second deflection section 42.

In one embodiment, the first deflection section 40 includes a coil wrapping 60, which may be a continuation of the coil wrapping 35 from the stiffening section 32 or it may be a separate coil wrapping (e.g. similarly constructed or otherwise). The coil wrapping 60 is disposed about the working lumen 18 and is preferably compression fitted around the inner liner 26.

Forming an exterior layer of the first deflection section 40 is a polymeric liner 62. The liner 62 is disposed about the coil wrapping 60 and is made of a polymeric material having a lower durometer than the durometer of the outer liner 58 of the stiffening section 32 to facilitate bending of the deflection section 40. In one example, the liner 62 of the first deflection section 40 has a Shore D durometer of between about 10 to 50 (preferably between about 25 and 40), and the liner 58 of the stiffening section 32 has a Shore D durometer of between about 50 and 90 (preferably between about 55 and 72). Medically acceptable thermoplastics and/or thermosets may be used to make the liner 62, such as for example, silicone, nylon, urethane, PTFE, a fluoropolymer, polyethylene, polypropylene, acetyl, urethane, and others.

The first deflection section 40 is configured to be "actively deflected" by an interventionalist. In one embodiment, the access sheath 10 comprises at least one control wire 46 moveably disposed in at least one of the additional lumens 22, 22', 24 and/or 24' for actively bending the first deflection section 40. The control wire 46 is connected at its distal end to the distal portion 16 of the elongated member 12 so that the tip 38 may be easily bent at an angle and maneuvered by the interventionalist. As illustrated, the additional lumens 22, 22', 24 and/or 24' do not extend through the tip 38, but rather terminate between the first deflection section 40 and the tip 38. The distal end of the control wire 46 is anchored within the distal portion 16 via an anchor or cannula 64 disposed in the additional lumens 22, 22', 24 and/or 24', so that when tension is applied to the control wire 46, the control wire 46 will cause the first deflection section 40 to bend at an angle to position the tip 38.

The proximal end of the control wire 46 may be joined to a control handle 66, such as for example, a integral thumb actuator as shown or a separate handle or otherwise, for manipulation of the control wire 46. The control wire 46 may be a single steel wire, or may be a wire bundle. Alternatively, the control wire 46 may use filaments made from other materials, such as nylons, polyesters, or other polymers, or polymer reinforced with glass, carbon, or metallic wires or fibers.

In one embodiment as illustrated, the control handle 66 has easy-to-use controls so that the interventionalist can readily adjust the position of the tip 38 via the first deflection section 40. A retainer 68 is preferably molded into the proximal portion 14 of the elongated member 12, or otherwise assembled in place. The retainer 68 has a base portion 70 and a curved rack of teeth 72. The base portion 70 also has a pivot point or pin 74. One aperture 76 is for access for the control wire 46 for assembly with the actuator 78. The actuator 78 includes a proximal portion 80 for interfacing with the hand or thumb of the interventionalist, and a distal portion 81 which mounts on the pivot pin 74. A spring (not shown) is operably disposed in the actuator 78 to allow the interventionalist to depress the proximal portion 80 and disengage a locking member 83, for example, from engagement with the rack of teeth 72 to allow pivoting of the actuator 78 on the pivot pin 74 to move the position of the actuator 78 on the rack of teeth 72, thereby moving the control wire 46 to bend the first deflection section 40. The proximal portion 80 can then be released by the interventionalist so that the spring moves the locking member 83 outwardly back into engagement with the curved rack of teeth 72 to lock the first deflection section 40 at a specific deflection position. Other suitable control handle arrangements may also be employed such as those disclosed in U.S. Patent Application Publication 2007/0203474 which is incorporated herein by reference in its entirety.

The access sheath 10 may include one or more control wires 46, preferably distributed radially across the proximal and distal portions 14 and 16 of the elongated member 12. For instance, the control wires 46 may be connected at radial intervals of 180°, 120°, or 90° if there are, respectively two, three, or four control wires 46. Alternatively and as illustrated in FIGS. 1c2, 1d2 and 1e2, two pairs of control wires 46 may be positioned such that each pair is on opposing sides of the access sheath 10 relative to the other pair, and each control wire 46 of a corresponding pair is spaced apart and adjacent to the other control wire 46 of the corresponding pair. Such an arrangement preferably facilitates maneuvering and positioning of the first deflection section 40. The first deflection section 40 is preferably sufficiently flexible to bend in response to actuation of the control handle 66 to an angle of at least 90° to position the tip 38. In other embodiments, the first deflection section 40 may be bent around and at angle of at least 180° or more, such as for example 225°-270° to position the tip 38.

The second deflection section 42 is configured to bend at a second angle to reposition the tip 38. In one embodiment, the second deflection section 42 uses "passive deflection" to bend at the second angle. That is, the second deflection section 42 bends in response to being contacted or bumped by an external object, such as for example, part of the patient's body. Alternatively, active deflection may be used to bend the second deflection section 42.

As illustrated, the second deflection section 42 includes a series articulating members 82 that are disposed about the working lumen 18 and around the inner liner 26. The articulating members 82 are pivotally connected to each other to bend the second deflection section 42 to the second angle. In one embodiment, the articulating members 82 are formed from a laser cut cannula 84. Each of the articulating members 82 has a positive feature 86 and a negative feature 88. The positive feature 86 of one articulating member 82 engages the negative feature 88 of the adjacent articulating member 82 to form a pivotal connection 90.

Forming an exterior layer of the second deflection section 42 is a polymeric liner 92 which covers the articulating members 82. The polymeric liner 92 is made of a polymeric material having a lower durometer than the durometer of the outer liner 58 of the stiffening section 32 to facilitate bending of the second deflection section 42. Preferably, the polymeric liner 92 is made of the same or similar polymeric material as the polymeric liner 62 of the first deflection section 40.

As shown in FIG. 1a, the second deflection 42 sections may be disposed immediately adjacent to the first deflection section 40. Alternatively and as illustrated in FIG. 1b, the second deflection section 42 may be spaced apart from the first deflection section 40. In the latter embodiment, an additional stiffening section 94 is disposed between the first and second deflection sections 40 and 42 for providing a particular positioning and reposition pattern (e.g. with pivotal reach) for the tip 38 that may well suited for navigating certain tortuous passageways. The additional stiffening section 94 preferable has the same or similar layer construction as the stiffening section 32 of the sheath's proximal portion 14 with either a coil-on-coil or a coil-on-braiding or vice versa reinforcement layer construction as described in detail in the foregoing paragraphs.

Figure 3A:
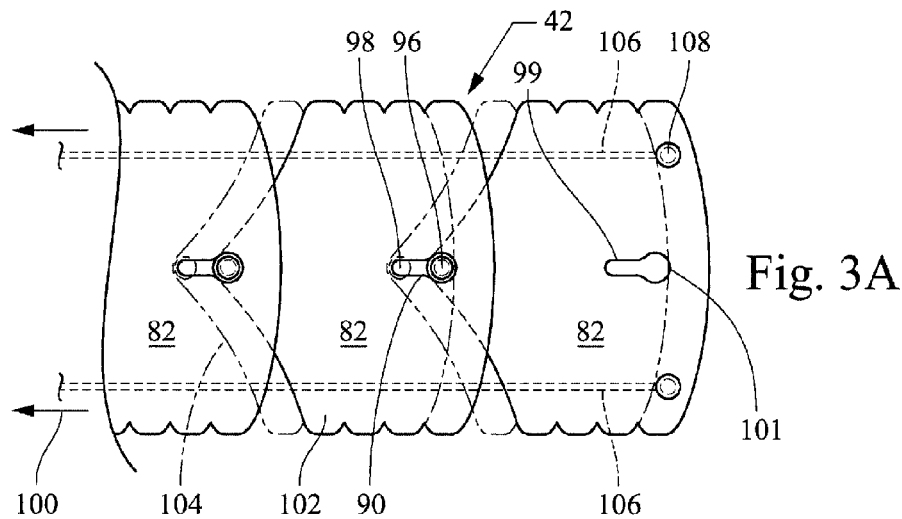
FIG. 3a is a side view of a portion of an access sheath in accordance with an embodiment of the present invention.

Referring to FIG. 3a, one embodiment for the second deflection section 42 is provided. As illustrated, the articulating members 82 each have a pin 96 and a slot 98. The pin 96 of one of the articulating members 82 engages the slot 98 of the adjacent articulating number 82 to form the pivotal connection 90. The articulating members 82 move axially 100 relative to each other from a relaxed position 102 to a compressed position 104 when a first deflection section 40 is actuated to bend. Notable, the axial movement 100 of the articulating members 82 to the compressed position 104 does not cause the second deflection section 42 to bend or substantially bend, but rather restrains pivotal movement of the articulating members 82, which is believed to concentrate or enhance the forces for bending the first deflection section 40.

Figure 3B:
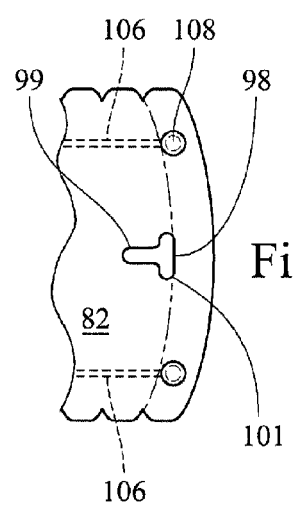
FIG. 3b is a side view of a portion of an access sheath in accordance with one embodiment of the present invention.
Figure 3C:
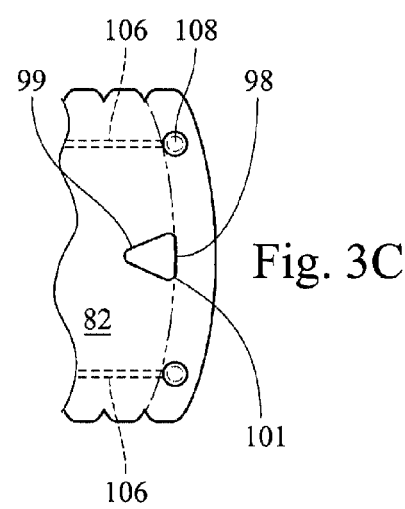
FIG. 3c is a side view of a portion of an access sheath in accordance with another embodiment of the present invention.

Referring also to FIGS. 3b and 3c, the slots 98 may be configured to facilitate pivotal movement in the relaxed position 102 and to restrain pivotal movement in the compressed position 104. In particular, the slots 98 may each have a relatively narrow proximal portion 99, which more tightly engages the pin 96 to restrain pivotal movement in the compressed position 104, and a relatively wider distal portion 101, which allows the pin 96 more freedom to move therein to facilitate pivotal movement in the relaxed position 102. For example, the proximal portion 99 may be configured as a narrow straight slot, and the distal portion 101 may be configured as a relatively wider circular opening extending from the proximal portion 99 as illustrated in FIG. 3a. Alternatively, the slots 98 may be configured as "T" or triangular openings as illustrated in FIGS. 3b and 3c, respectively.

Figure 3D:
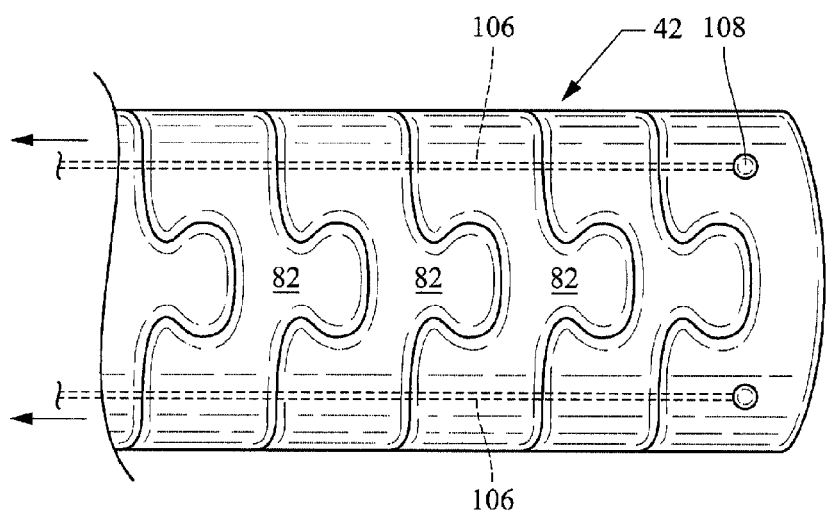
FIG. 3d is a side view of a portion of an access sheath in accordance with one embodiment of the present invention.

In at least one embodiment and as illustrated in FIGS. 3a and 3d, at least one additional control wire 106 is provided for facilitating axial movement 100 of the articulating members 82 to the compressed position 104. Each additional control wire 106 is preferably movably disposed in one of the additional lumens. Also referring to FIGS. 1a-1b, the additional control wire 106 has one end 108 connected to one of the articulating members 82 positioned distally in the series of articulating members 82 and the other end 110 operably connected to a second retainer-actuator arrangement 112 of the control handle 66 for moving the articulating members 82 proximally to the compressed position 104. The second retainer-actuator arrangement 112 operates the same as or similar to the retainer-actuator arrangement 68, 70, 72, 74, 76 and 78 as discussed previously. The additional control wire 106 may also include a spring 114 disposed between the two ends 108 and 110 to facilitate the articulating members 82 moving distally from the compressed position 104 to pivot when a portion of elongated member 12 contacts an external object.

Figure 4A:
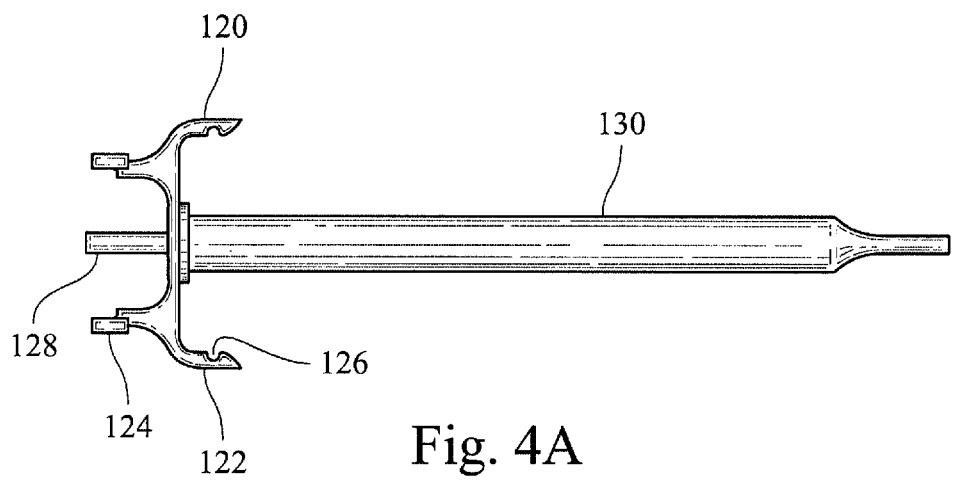
FIG. 4a is a side view of an insert for use with an access sheath in accordance with an embodiment of the present invention.
Figure 4B:
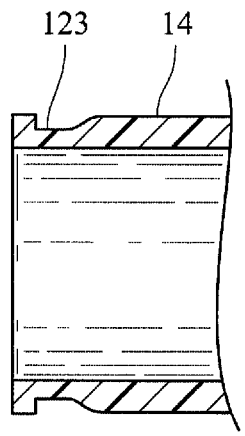
FIG. 4b is a partial cross-sectional view of a proximal portion of an access sheath for interfacing with the insert depicted in FIG. 4a in accordance with one embodiment of the present invention.

Referring to FIGS. 4a through 4b, an insert 120 for use with the access sheath 10 is provided. The insert 120 is meant to clip onto the proximal portion 14 of the access sheath 10 using the interface 122 and a mating proximal portion 123 of the access sheath 10 as shown in FIG. 4b. The interface 122 is operated by a finger lever 124, the interventionalist squeezing the levers 124 to part the interface portions 122 in order to apply the interface 122 to the access sheath 10. The interventionalist then releases the levers 124, allowing the interface portions 122 and notches 126 to latch the mating proximal portion 123 of the access sheath 10.

The interface 122 may include control portion 128 and may also include diagnostic or a therapeutic device 130, such as a retriever for kidney stones or a laser fiber for breaking up calculi in a kidney or other organ. The control portion 128 may be a control rod, or other connection for the desired diagnostic or therapeutic device 130. The control portion 128 is used to manipulate the device 140, e.g., extending and retracting a retrieval basket for removing kidney stones.

Figure 4C:
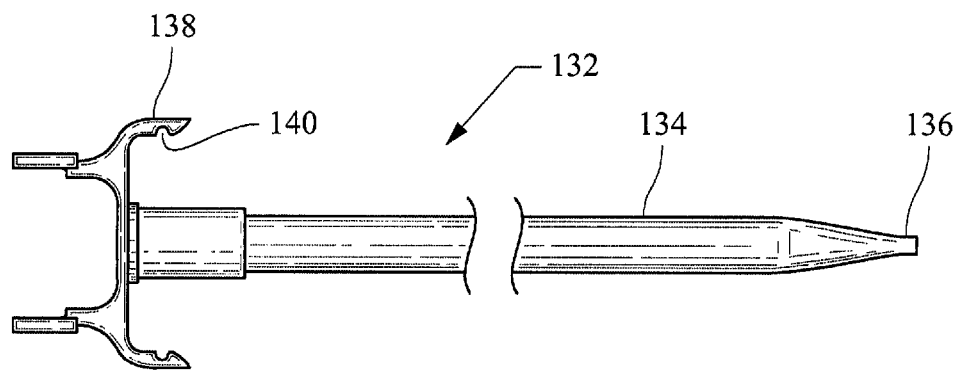
FIG. 4c is an obturator for use with an access sheath in accordance with another embodiment in the present invention.

Referring to FIGS. 4b-4c, an obturator 132 is useful in deploying the access sheath 10 into a patient. The obturator 132 occupies the working lumen 18 of the sheath 10, preventing its collapse during deployment. Alternatively, the obturator 132 may be used after deployment in order to expand the working lumen 18. The obturator 18 extends from the proximal portion 14 to the distal portion 16 of the access sheath 10. The obturator 132 includes a main shaft 134, a distal tip 136, and a proximal portion 138. The distal tip 136 may be tapered as shown for easy introduction. The proximal portion 138 preferably includes an engaging portion or connector 140 for removeably clipping or attaching to the mating portion 123 of the proximal portion 14 of the access sheath 10.

Figure 2A:
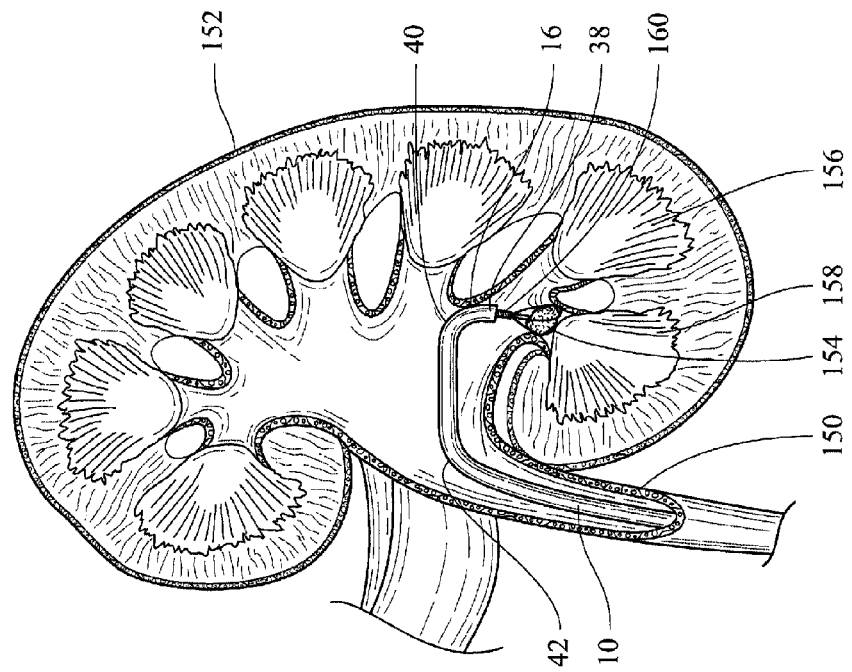
FIG. 2a is an environmental view of an access sheath in accordance with an embodiment of the present invention.
Figure 2B:
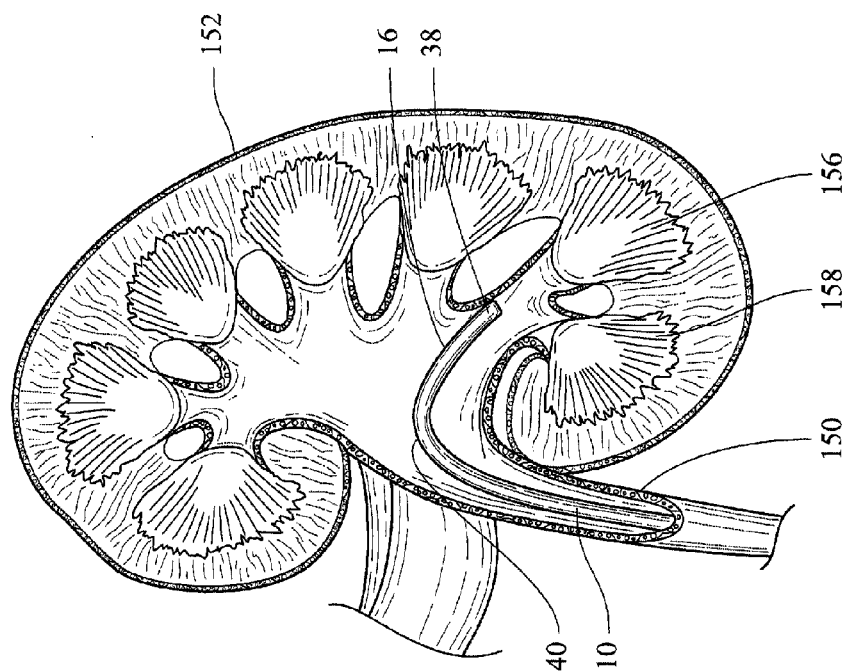
FIG. 2b is an environmental view of an access sheath in accordance with one embodiment of the present invention.
Figure 5:
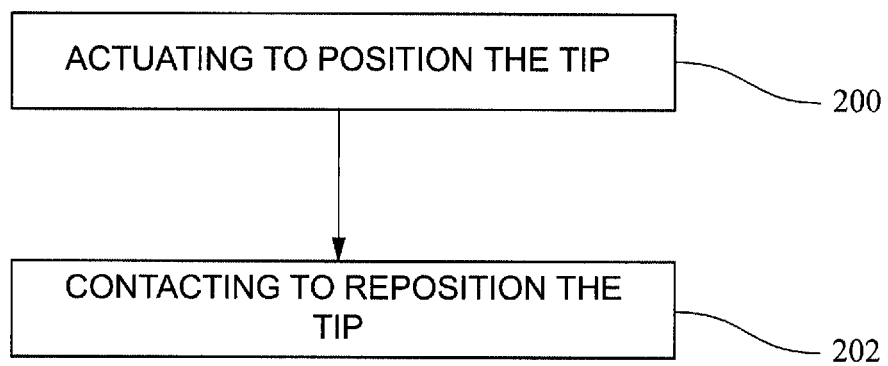
FIG. 5 is an example of a method for positioning an access sheath in a patient's body in accordance with the present invention.

Referring to FIGS. 2a-2b and 5, an example of a method for positioning an access sheath in a patient's body by an interventionalist is provided. As illustrated, the access sheath 10 is advanced through the ureter 150 to access the kidney 152 of the patent for kidney stone 154 removal. The first deflection section 40 is actuated (at 200) to bend at a first angle to position the tip 38 adjacent to the lower, outboard calyx 156. The distal portion 16 of the access sheath 10 is contacted with or bumped against (at 202) the kidney 152 to produce a force that bends the second deflection section 42 at a second angle, repositioning the tip 38 (e.g. with pivotal reach) into the lower, inboard calyx 158 where, in this example, the kidney stone 154 is located. A retrieval device 160 is deployed out the working lumen to remove the kidney stone 154.

As a person skilled in the art will readily appreciate, the above description is meant as an illustration of the implementation of the principles of this invention. This description is not intended to limit the scope of application for this invention and that the invention is susceptible for modification, variation and change, without departing from the spirit of this invention, as defined in the following claims.

The invention claimed is:

1. An access sheath for being positioned in a patient's body by an interventionalist, the access sheath comprising:
an elongated member having a proximal portion extending to a distal portion and a plurality of lumens formed therethrough including a working lumen and a first additional lumen, the first additional lumen is configured to receive one of an optical system and an irrigation system, the proximal portion having a stiffening section including a first coil and one of a first braiding and a second coil, the first coil and the one of the first braiding and the second coil are disposed about the working lumen in concentric relationship with each other, the distal portion having a tip and a first deflection section and a second deflection section, the first deflection section is proximal to the tip and distal to the second deflection section, the first deflection section is configured to be actuated by the interventionalist to bend at a first angle to position the tip, and the second deflection section is configured to bend at a second angle to reposition the tip, wherein the second deflection section includes an axial series of articulating members disposed about the working lumen, the articulating members being axially movable relative to each other between a compressed position and a relaxed position, each of the articulating members having a pin adjacent one axial end of the articulating member and a slot adjacent the other axial end of the articulating member, the pin of one of the articulating members engaging the slot of the adjacent articulating member to form a pivotal connection, wherein at least one of the slots has a relatively narrow portion that tightly engages the pin in the compressed position and restrains a pivotal movement between the pin and the slot, and a relatively wider portion extending from the relatively narrow proximal portion, wherein the pin resides in the relatively wider portion in the relaxed position, which freely allows the pivoting movement between the pin and the slot.

2. The access sheath according to claim 1 wherein the first deflection section includes a third coil disposed about the working lumen and the first and second deflection sections include a first polymeric material forming an exterior layer of the distal portion about the third coil, and the stiffening section includes a second polymeric material forming an exterior layer of the proximal portion about the first coil and the one of the first braiding and the second coil, the first polymeric material having a lower durometer than the second polymeric material.

3. The access sheath according to claim 1 wherein the second deflection section uses passive deflection to bend at the second angle in response to a portion of the elongated member contacting part of the patient's body.

4. The access sheath according to claim claim 1, wherein the articulating members move axially relative to each other from a relaxed position to a compressed position when the first deflection section is actuated to bend, and in the compressed position pivotal movement of the articulating members is restrained.

5. The access sheath according to claim 4 further comprising:
a control handle connected to the proximal portion of the elongated member; and
a first control wire, the elongated member having a second additional lumen and the first control wire being movably disposed in the second additional lumen, the first control wire having one end connected to one of the articulating members positioned distally in the series of the articulating members and the other end is operably connected to the control handle for moving the articulating members proximally to the compressed position when the control handle is actuated.

6. The access sheath according to claim 5 wherein the first control wire includes a spring disposed between the two ends to facilitate the articulating members moving distally from the compressed position and pivoting when the portion of the elongated member contacts the part of the patient's body.

7. The access sheath according to claim 1 further comprising:
a control handle connected to the proximal portion of the elongated member; and
a first and a second control wire, the elongated member having a second and third additional lumen and the second control wire being movably disposed in the third additional lumen, the second control wire having one end connected to the distal portion of the elongated member between the first deflection section and the tip and the other end operably connected to the control handle for bending the first deflection section when the control handle is actuated.

8. The access sheath according to claim 1 wherein the distal portion has a stiffening section disposed between the first and second deflection sections, the stiffening section of the distal portion including a fourth coil and one of a second braiding and a fifth coil, the fourth coil and the one of the second braiding and the fifth coil are disposed about the working lumen in concentric relationship with each other.

9. A medical kit for providing internal access to a patient's body by an interventionalist, the kit comprising:
an optical system for viewing; and
an access sheath for being positioned in the patient's body, the access sheath including:

an elongated member having a proximal portion extending to a distal portion and a plurality of lumens formed therethrough including a working lumen and a first additional lumen, the first additional lumen is configured to receive the optical system, the proximal portion having a stiffening section including a first coil and one of a first braiding and a second coil, the first coil and the one of the first braiding and the second coil are disposed about the working lumen in concentric relationship with each other, the distal portion having a tip and a first deflection section and a second deflection section, the first deflection section is proximal to the tip and distal to the second deflection section, the first deflection section is configured to be actuated by the interventionalist to bend at a first angle to position the tip, and the second deflection section is configured to bend at a second angle to reposition the tip, wherein the second deflection section includes an axial series of articulating members disposed about the working lumen, the articulating members being axially movable relative to each other between a compressed position and a relaxed position, each of the articulating members having a pin adjacent one axial end of the articulating member and a slot adjacent the other axial end of the articulating member, the pin of one of the articulating members engaging the slot of the adjacent articulating member to form a pivotal connection, wherein at least one of the slots has a relatively narrow portion that tightly engages the pin in the compressed position and restrains a pivotal movement between the pin and the slot, and a relatively wider portion extending from the relatively narrow proximal portion, wherein the pin resides in the relatively wider portion in the relaxed position, which freely allows the pivoting movement between the pin and the slot.

* * * * *

UNITED STATES PATENT AND TRADEMARK OFFICE
CERTIFICATE OF CORRECTION

PATENT NO. : 8,758,231 B2  
APPLICATION NO. : 13/319850  
DATED : June 24, 2014  
INVENTOR(S) : Tyler J. Bunch et al.

Page 1 of 1

It is certified that error appears in the above-identified patent and that said Letters Patent is hereby corrected as shown below:

In the Claims

In column 9, line 58, after "members having a" replace "in" with --pin--.

Signed and Sealed this  
Seventh Day of April, 2015

Michelle K. Lee  
*Director of the United States Patent and Trademark Office*